(12) United States Patent
Bohl et al.

(10) Patent No.: US 8,656,755 B2
(45) Date of Patent: Feb. 25, 2014

(54) MEASURING DEVICE FOR DETECTING MOISTURE AND TEMPERATURE OF A FLOWING MEDIUM

(75) Inventors: Benjamin Bohl, Berlin (DE); Peter Balzer, Berlin (DE)

(73) Assignee: EPCOS AG, Munich (DE)

( * ) Notice: Subject to any disclaimer, the term of this patent is extended or adjusted under 35 U.S.C. 154(b) by 559 days.

(21) Appl. No.: 12/876,462

(22) Filed: Sep. 7, 2010

(65) Prior Publication Data

US 2011/0030461 A1 Feb. 10, 2011

Related U.S. Application Data

(63) Continuation of application No. PCT/EP2009/053026, filed on Mar. 13, 2009.

(30) Foreign Application Priority Data

Mar. 19, 2008 (DE) .......................... 10 2008 014 926
Jun. 24, 2008 (DE) .......................... 10 2008 029 793

(51) Int. Cl.
*G01N 19/10* (2006.01)
*G01K 1/16* (2006.01)
*G01K 13/02* (2006.01)

(52) U.S. Cl.
USPC ...................... 73/29.01; 374/142; 374/E1.018

(58) Field of Classification Search
USPC ............. 73/25.04, 29.01, 29.05; 374/E1.018, 374/E1.019, E1.023, 142, 208
See application file for complete search history.

(56) References Cited

U.S. PATENT DOCUMENTS

| | | | | |
|---|---|---|---|---|
| 4,028,942 A | * | 6/1977 | Gardiner | 73/335.02 |
| 4,170,455 A | * | 10/1979 | Henrie | 436/144 |
| 5,691,466 A | * | 11/1997 | Lawrence et al. | 73/29.05 |
| 6,030,116 A | * | 2/2000 | Yanai et al. | 374/142 |
| 6,361,206 B1 | * | 3/2002 | Bonne | 374/138 |
| 6,571,623 B1 | * | 6/2003 | Blasczyk et al. | 73/204.22 |
| 6,805,483 B2 | * | 10/2004 | Tomlinson et al. | 374/144 |
| 7,104,117 B2 | | 9/2006 | Büttgenbach et al. | |
| 2004/0007049 A1 | * | 1/2004 | Hoppach | 73/29.02 |
| 2004/0250606 A1 | | 12/2004 | Buttgenbach et al. | |
| 2009/0207878 A1 | | 8/2009 | Bard et al. | |
| 2009/0217736 A1 | * | 9/2009 | Chan et al. | 73/25.04 |
| 2013/0008232 A1 | * | 1/2013 | Bergsten | 73/29.01 |

FOREIGN PATENT DOCUMENTS

| | | |
|---|---|---|
| DE | 41 30 063 A1 | 3/1993 |
| DE | 101 52 777 A1 | 5/1993 |
| DE | 100 24 490 A1 | 1/2002 |
| DE | 103 36 690 A1 | 3/2005 |
| DE | 10 2006 021 528 B3 | 9/2007 |
| DE | 10 2007 007 215 A1 | 8/2008 |
| EP | 0 726 450 A1 | 8/1996 |
| EP | 1 696 184 A2 | 8/2006 |

(Continued)

*Primary Examiner* — Lisa Caputo
*Assistant Examiner* — Punam Roy
(74) *Attorney, Agent, or Firm* — Slater & Matsil, L.L.P.

(57) ABSTRACT

A measuring device for detecting the amount of moisture in and the temperature of a flowing medium is disclosed. Flow-directing elements which mix the flowing medium and direct it in a desired direction are arranged in the measuring device. The average temperature of the medium can thus be detected using a suitably arranged temperature sensor. In addition, the moisture sensor may be arranged in such a manner that a selective amount of moisture in the medium is detected.

18 Claims, 2 Drawing Sheets

(56) References Cited

FOREIGN PATENT DOCUMENTS

| | | |
|---|---|---|
| FR | 2 750 771 A1 | 1/1998 |
| JP | 2005-507497 A | 3/2005 |
| WO | WO 02/16908 A1 | 2/2002 |
| WO | WO 2006/087909 A1 | 8/2006 |
| WO | WO 2007/079516 A2 | 7/2007 |

\* cited by examiner

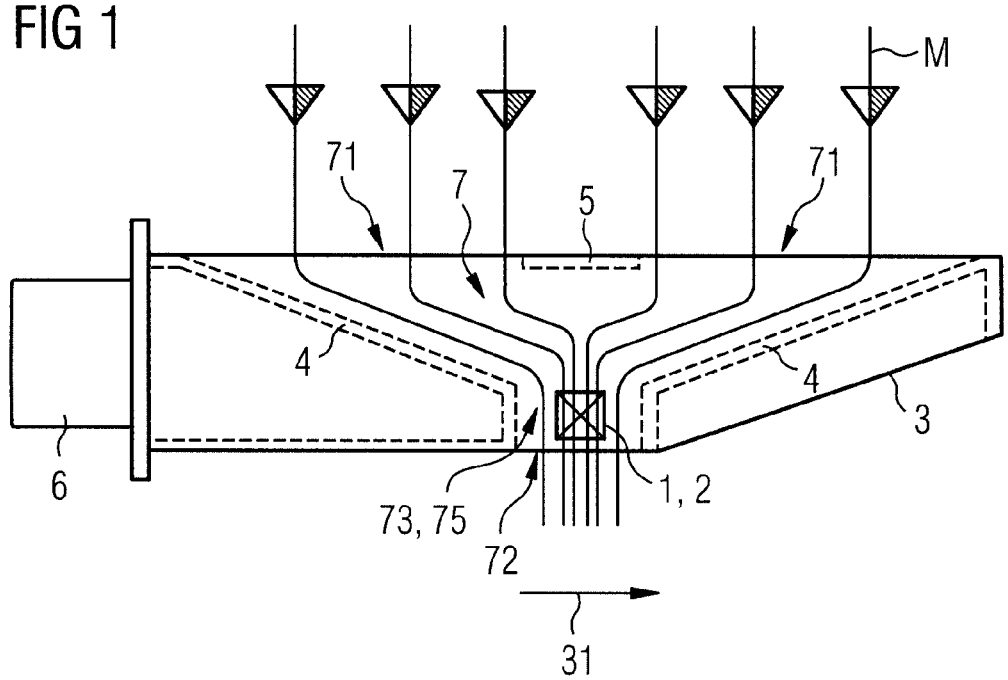

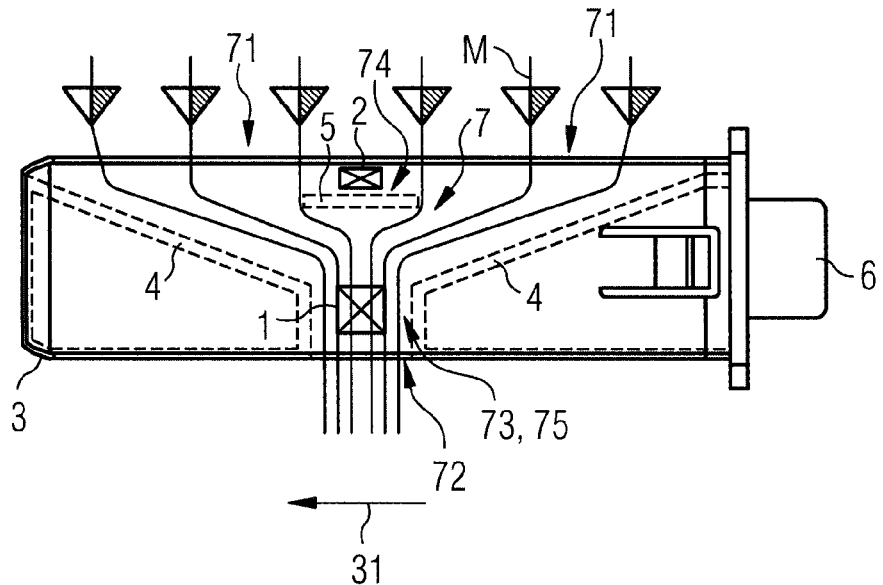
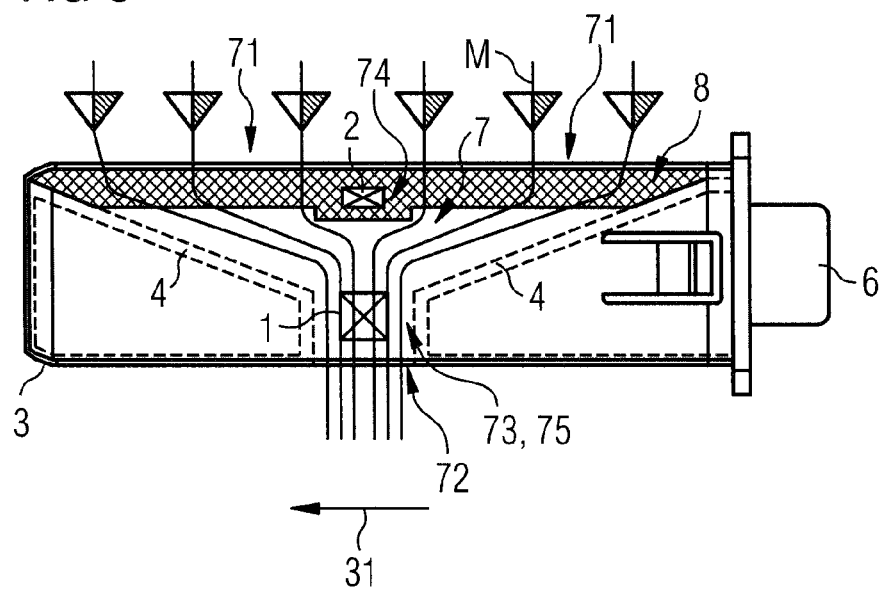

MEASURING DEVICE FOR DETECTING MOISTURE AND TEMPERATURE OF A FLOWING MEDIUM

This application is a continuation of co-pending International Application No. PCT/EP2009/053026, filed Mar. 13, 2009, which designated the United States and was not published in English, and which claims priority to German Application No. 10 2008 014 926.8, filed Mar. 19, 2008, and German Application No. 10 2008 029 793.3, filed Jun. 24, 2008, each of which is incorporated herein by reference in its entirety.

TECHNICAL FIELD

A measuring device for measuring the moisture content of a flowing medium is specified.

BACKGROUND

German patent document DE 10 2006 021 528 B3 describes a sensor for measuring the temperature of an air flow.

SUMMARY

Aspects of the invention disclose a device to determine the moisture content of a flowing medium as simply as possible.

A measuring device which has a moisture sensor for detecting the amount of moisture in a flowing medium is specified. The moisture sensor is arranged on a carrier. A temperature sensor which can detect the temperature of the medium is also preferably situated on the carrier.

The carrier preferably has flow-directing elements which are suitable for directing the flowing medium in the direction of one or both sensors.

For example, the carrier has a channel having an inlet opening and an outlet opening for the flowing medium. The flow-directing elements may be situated inside the channel, for example, in the form of deflecting surfaces or groove-like depressions.

In one preferred embodiment, the flow-directing elements are designed and arranged in such a manner that the moisture sensor can detect the average amount of moisture in the medium.

The flow-directing elements concentrate the flowing medium in the direction of the sensor, for example. This means that different partial flows, in particular, those parts of the flowing medium which run on the edge of the flow, are combined and are led in the direction of the sensor.

For example, the flowing medium can be concentrated by the tapering of the cross section of a channel along the direction of flow of the medium. In this case, the medium flows through the inlet opening into the channel and is led by the flow-directing elements to a constricted region whose cross section is smaller than the cross section of the inlet opening. This results in partial flows of the medium being combined. In one embodiment, the medium is compressed by the constriction of the channel and strikes the moisture sensor in compressed form. The average amount of moisture in the medium in its uncompressed form can be derived from the measured amount of moisture in the medium in its compressed form.

The channel may be in the form of a funnel. For example, the moisture sensor is situated in the region of the funnel neck in which the flowing medium is present in concentrated form.

As an alternative or in addition to concentrating the medium, the flow-directing elements may mix a volume of the medium flowing past. The medium is preferably not compressed in this case.

In another embodiment, the flow-directing elements and the moisture sensor are arranged in such a manner that the medium is directed in the direction of the moisture sensor without being concentrated or mixed. The moisture sensor can then selectively determine the amount of moisture in the medium. In this case, the term "selectively" means that the amount of moisture in the medium in its unconcentrated form is detected at one point.

For this purpose, the moisture sensor is arranged in a region of the measuring device in which the flowing medium is present in unconcentrated and unmixed form. For example, the moisture sensor is arranged in a non-constricted region of a channel in which the cross section is equal to the cross section of the inlet opening. The moisture sensor may also be directly arranged at the inlet of the channel.

Like the moisture sensor, the temperature sensor may be arranged in such a manner that it can detect an average or selective temperature of the medium.

In one embodiment, the temperature sensor and the moisture sensor are integrated in a common sensor element.

With this arrangement, the amount of moisture in the medium and the temperature of the medium can be detected in a simple manner at the same point.

In an alternative embodiment, the temperature sensor and the moisture sensor are in the form of separate components. These components may be arranged at different points of the carrier.

With this embodiment, the moisture sensor, for example, can determine the average amount of moisture in the medium, whereas the temperature sensor detects a selective temperature of the medium. For this purpose, the moisture sensor is arranged in a region of the carrier in which a concentrated or mixed volume of the medium flows. The temperature sensor may be arranged in a region of the carrier in which the medium flowing past is not concentrated and is not mixed. For example, the temperature sensor is arranged at the inlet of a channel and the moisture sensor is arranged in a constricted region of the channel which has a smaller cross section than the inlet opening.

In an alternative embodiment, the moisture sensor and the temperature sensor are arranged in such a manner that the amount of moisture in the medium is selectively detected and the temperature of the medium is detected in a manner averaged over a volume.

The device may also have elements containing a thermally conductive material. These elements are arranged in the measuring device in such a manner that the flowing medium at least partially flows around or through them. In this case, the thermal conductivity of the material should be so large that an average temperature is established within a short period of time at least in a partial region of the element, which temperature corresponds to the average temperature of the flowing medium or from which the average temperature of the medium can be derived in a simple manner. For example, the element projects into a channel of the measuring device and the medium partially flows around the element. In one embodiment, the element is in the form of a grating which is situated in a channel of the measuring device and extends over the cross section of the channel.

The temperature sensor is preferably thermally connected to this element and detects the temperature of the element. As a result, an average temperature of the medium can be determined in a simple manner without the medium having to be concentrated or mixed. In addition, the temperature sensor then no longer needs to be arranged in a region of the measuring device, past which the medium directly flows, and is thus better protected against mechanical damage.

Elements for shielding the moisture sensor or the temperature sensor are preferably provided in the measuring device. These elements may be arranged above the sensor element, for example at an inlet opening of the measuring device.

The shielding elements prevent the medium from directly impinging on the sensor element. This is used, on the one hand, to protect the sensor element. The shielding element may also ensure that the medium is concentrated or mixed before it strikes the sensor element. This is advantageous, in particular, when determining the average amount of moisture or the average temperature.

In one preferred embodiment, a sensor element is connected to an electronic circuit which converts a sensor signal into other electronic signals, for example, current, voltage, frequency or digital protocols. For this purpose, the sensor element is arranged on a printed circuit board, for example, and is connected to the electronic circuit.

The electronic circuit is preferably designed in such a manner that the sensor element can be calibrated. If the medium impinges on the moisture sensor in the form of a compressed volume, the correct value for the average amount of moisture in the medium in its uncompressed form can be output, for example, by means of suitable calibration.

In one preferred embodiment, the flowing medium is a flowing gas, in particular, air.

BRIEF DESCRIPTION OF THE DRAWINGS

The specified measuring device and its advantageous refinements are explained below using diagrammatic figures which are not true to scale and in which:

FIG. 1 shows a cross section of a measuring device having a moisture sensor and a temperature sensor integrated therein;

FIG. 2 shows a cross section of a measuring device having a moisture sensor and a separate temperature sensor; and FIG. 3 shows a cross section of a measuring device having a moisture sensor and a separate temperature sensor which is surrounded by an element made of a thermally conductive material.

The following list of reference symbols may be used in conjunction with the drawings:

1 Moisture sensor
2 Temperature sensor
3 Carrier
31 Longitudinal axis of the carrier
4 Flow-directing element
5 Shielding element
6 Connector
7 Channel
71 Inlet opening
72 Outlet opening
73 Constricted region
74 Non-constricted region
75 Funnel neck
8 Element made of thermally conductive material
M Flowing medium

DETAILED DESCRIPTION OF ILLUSTRATIVE EMBODIMENTS

FIG. 1 shows a measuring device through which a flowing medium M flows. The measuring device has a carrier 3, the longitudinal axis 31 of which is oriented perpendicular to the direction of flow (arrows) of the flowing medium M. A channel 7 having an inlet opening 71 and an outlet opening 72 is situated in the measuring device. A moisture sensor 1, in which a temperature sensor 2 is integrated, is arranged in the channel. The flowing medium M flows through the inlet opening 71 into the measuring device, past the sensors 1, 2 and out of the measuring device through the outlet opening 72.

The medium M is concentrated in the direction of the sensors 1, 2 by means of flow-directing elements 4. The flow-directing elements 4 are in the form of deflecting surfaces which are tilted with respect to the longitudinal axis 31 of the carrier 3. They form a funnel, in the neck 75 of which the sensors 1, 2 are situated. The funnel-shaped arrangement directs the inflowing medium M in the direction of the sensors 1, 2. Since the funnel tapers in the direction of the sensor elements 1, 2, partial flows of the medium M are combined in the direction of the funnel neck 75 and are preferably mixed. The sensors 1, 2 which are situated in a constricted region 73 of the channel 7 can thus detect the average amount of moisture in the medium M and the average temperature of the medium M.

A shielding element 5 which shades the sensors 1, 2 is arranged at the inlet opening 71 of the channel 7. The shielding element 5 prevents the inflowing medium M from flowing directly onto the sensors 1, 2.

The measuring device can be electrically connected by means of a connector 6. The connector 6 is in electrical contact with the sensors 1, 2, for example by means of a printed circuit board. When electrically connecting the measuring device, the measurement data acquired are preferably also output and processed further.

FIG. 2 shows a measuring device in which the moisture sensor 1 and the temperature sensor 2 are arranged in different regions of a channel 7. As in FIG. 1, the channel 7 is in the form of a funnel in this case. The moisture sensor 1 is again arranged in the funnel neck 75 and is used to determine the average amount of moisture in the flowing medium M. The moisture sensor 1 is protected from a direct flow of the medium M by a shielding element 5. The temperature sensor 2 is situated on that side of the shielding element 5 which is opposite the moisture sensor 1, and the medium M flows directly onto the temperature sensor 2. The temperature sensor 2 is arranged at the level of the inlet opening 71. The medium M is present in unconcentrated or unmixed form in this non-constricted region 74. A selective temperature of the flowing medium M can thus be determined at this point, that is to say the temperature is not averaged over a volume.

FIG. 3 shows a measuring device having a channel 7 in the form of a funnel, in which device the moisture sensor 1 is arranged in the funnel neck 75. The temperature sensor 2 is situated in the region of the inlet opening 71 and is surrounded by a grating 8 which contains a thermally conductive material. The grating 8 extends over the cross section of the inlet opening 71 of the channel 7 and the flowing medium M flows through the grating. The grating 8 is heated in the process. On account of the good thermal conductivity of the grating 8, an average temperature is established within a short period of time in the region of the temperature sensor 2. The temperature sensor 2 measures this temperature and can use it to determine the temperature of the flowing medium M averaged over the cross section of the inlet opening 71. In addition, the grating 8 mixes the medium M and thus also constitutes a flow-directing element. A shielding element 5 is preferably integrated in the grating 8 and shades the moisture sensor 1 and the temperature sensor 2.

In an alternative embodiment, the temperature sensor 2 may also be arranged outside the channel 7, with the result that it does not come into contact with the flowing medium M.

Although described using the exemplary embodiments, the invention is not restricted to the exemplary embodiments but rather comprises any new feature and any combination of features. This includes, in particular, any combination of features in the patent claims even if this feature or this combination itself is not explicitly stated in the patent claims or exemplary embodiments.

What is claimed is:

1. A measuring device comprising:
    a moisture sensor for detecting an amount of moisture in a flowing medium;
    a temperature sensor for detecting a temperature of the flowing medium; and
    a carrier, the moisture sensor and the temperature sensor arranged on the carrier, the carrier having flow-directing elements, wherein the carrier has a channel having an inlet opening configured to receive the flowing medium flowing into the channel, wherein the channel has a constricted region with a cross section that is smaller than a cross section of the inlet opening, wherein the channel is in the form of a funnel and has a funnel neck, and wherein the moisture sensor is arranged in a region of the inlet opening and the temperature sensor is arranged in a region of the funnel neck or wherein the temperature sensor is arranged in a region of the inlet opening and the moisture sensor is arranged in a region of the funnel neck.

2. The measuring device as claimed in claim 1, wherein the flow-directing elements are suitable for directing the flowing medium in a direction of the moisture sensor and/or the temperature sensor.

3. The measuring device as claimed in claim 2, wherein the flow-directing elements are suitable for concentrating the flowing medium.

4. The measuring device as claimed in claim 1, wherein the flow-directing elements are suitable for mixing the flowing medium.

5. The measuring device as claimed in claim 1, wherein the moisture sensor is arranged in a region of the inlet opening and the temperature sensor is arranged in a region of the funnel neck.

6. The measuring device as claimed in claim 1, wherein the temperature sensor is arranged in a region of the inlet opening and the moisture sensor is arranged in a region of the funnel neck.

7. The measuring device as claimed in claim 1, further comprising an element that comprises a thermally conductive material and is thermally connected to the temperature sensor.

8. The measuring device as claimed in claim 7, wherein the element comprises a grating through which the flowing medium flows.

9. The measuring device as claimed in claim 1, further comprising a shielding element that prevents the flowing medium from flowing directly onto the moisture sensor and/or the temperature sensor.

10. The measuring device as claimed in claim 1, wherein the flowing medium comprises air.

11. A method comprising:
    locating a measuring device in a flowing medium;
    directing the flowing medium toward a temperature sensor and a moisture sensor using flow-directing elements within the measuring device, the temperature sensor and moisture sensor arranged on a common carrier of the measuring device;
    detecting an amount of moisture in the flowing medium using the moisture sensor; and
    detecting a temperature of the flowing medium using the temperature sensor,
    wherein the carrier has a channel having an inlet opening through which the flowing medium flows into the channel, wherein the channel is in the form of a funnel and has a funnel neck, and wherein the moisture sensor is arranged in a region of the inlet opening and the temperature sensor is arranged in a region of the funnel neck or wherein the temperature sensor is arranged in a region of the inlet opening and the moisture sensor is arranged in a region of the funnel neck.

12. The method of claim 11, wherein directing the flowing medium comprises concentrating the flowing medium.

13. The method of claim 11, wherein directing the flowing medium comprises mixing the flowing medium.

14. The method of claim 11, wherein directing the flowing medium comprises preventing the flowing medium from flowing directly onto the moisture sensor and/or the temperature sensor.

15. A measuring device comprising:
    a moisture sensor for detecting an amount of moisture in a flowing medium;
    a temperature sensor for detecting a temperature of the flowing medium; and
    a carrier, the moisture sensor and the temperature sensor arranged on the carrier, the carrier having flow-directing elements, wherein the carrier has a channel having an inlet opening through which the flowing medium flows into the channel, wherein the channel has a non-constricted region whose cross section is equal to a cross section of the inlet opening, the moisture sensor and/or the temperature sensor being arranged in the non-constricted region; and
    an element comprising a thermally conductive material and thermally connected to the temperature sensor.

16. A measuring device comprising:
    a moisture sensor for detecting an amount of moisture in a flowing medium;
    a temperature sensor for detecting a temperature of the flowing medium;
    a carrier, the moisture sensor and the temperature sensor arranged on the carrier, the carrier having flow-directing elements; and
    an element that comprises a thermally conductive material and is thermally connected to the temperature sensor.

17. The measuring device as claimed in claim 16, wherein the element comprises a grating through which the flowing medium flows.

18. A measuring device comprising:
    a moisture sensor for detecting an amount of moisture in a flowing medium;
    a temperature sensor for detecting a temperature of the flowing medium; and
    a carrier, the moisture sensor and the temperature sensor arranged on the carrier, the carrier comprising flow-directing elements, wherein the flow-directing elements are suitable for concentrating the flowing medium, and wherein the flow-directing elements concentrate the flowing medium in the direction of the moisture sensor and/or the temperature sensor; and
    an element that comprises a thermally conductive material and is thermally connected to the temperature sensor.

* * * * *